(12) United States Patent
Wang et al.

(10) Patent No.: US 12,166,176 B2
(45) Date of Patent: Dec. 10, 2024

(54) ELECTROLYTE SOLUTION ADDITIVE CONTAINING ISOCYANATE AND SULFAMIDE STRUCTURAL GROUPS AND APPLICATION THEREOF

(71) Applicant: Valiant Co., Ltd, Yantai (CN)

(72) Inventors: Huanjie Wang, Yantai (CN); Yu Shi, Yantai (CN); Cunsheng Lin, Yantai (CN); Shanguo Zhang, Yantai (CN); Liqi Xuan, Yantai (CN); Heng Jiang, Yantai (CN)

(73) Assignee: Valiant Co., Ltd, Yantai (CN)

( * ) Notice: Subject to any disclaimer, the term of this patent is extended or adjusted under 35 U.S.C. 154(b) by 0 days.

(21) Appl. No.: 18/487,142

(22) Filed: Oct. 16, 2023

(65) Prior Publication Data

US 2024/0097191 A1    Mar. 21, 2024

Related U.S. Application Data

(63) Continuation of application No. PCT/CN2022/078800, filed on Mar. 2, 2022.

(30) Foreign Application Priority Data

Nov. 24, 2021    (CN) .......................... 202111400107.1

(51) Int. Cl.
| | |
|---|---|
| H01M 10/0567 | (2010.01) |
| C07C 307/06 | (2006.01) |
| C07D 339/06 | (2006.01) |
| C07D 339/08 | (2006.01) |
| H01M 10/0525 | (2010.01) |

(52) U.S. Cl.
CPC ....... *H01M 10/0567* (2013.01); *C07C 307/06* (2013.01); *C07D 339/06* (2013.01); *C07D 339/08* (2013.01); *H01M 10/0525* (2013.01); *H01M 2300/004* (2013.01)

(58) Field of Classification Search
CPC ......... H01M 10/0567; H01M 10/0525; H01M 2300/004; C07C 307/06; C07D 339/06; C07D 339/08
See application file for complete search history.

(56) References Cited

U.S. PATENT DOCUMENTS

| | | | |
|---|---|---|---|
| 3,917,635 A | 11/1975 | Horlein et al. | |
| 3,931,277 A * | 1/1976 | Lohaus ................. | C07C 317/46 548/308.4 |
| 5,022,916 A | 6/1991 | Willms et al. | |
| 5,129,941 A | 7/1992 | Loher et al. | |
| 6,905,762 B1 * | 6/2005 | Jow .................... | H01M 10/0567 429/324 |
| 2016/0013517 A1 * | 1/2016 | Nakazawa ............ | H01M 4/463 429/188 |
| 2020/0127321 A1 * | 4/2020 | Kim .................. | H01M 10/0567 |
| 2020/0181071 A1 * | 6/2020 | Kozelj .............. | H01M 10/0568 |

FOREIGN PATENT DOCUMENTS

CN    114069049 A    2/2022

OTHER PUBLICATIONS

The decision of JPO to grant a Patent for Application JP2023546182 (Year: 2024).*
Internation Search Report of PCT/CN2022/078800, Mailed Aug. 4, 2022.
A. Blaschette et al., Phosphorus, Sulfur, and Silicon and the Related Elements, Polysulfonylamine: Teil XXXIV.1 Dimesylaminosulfonylisocyanat: Darstellung, Festkörperstruktur Und Additionsreaktionen Mit Alkoholen, vol. 70, pp. 91-97, 1992, UK.
J. Dalluhnet al., Phosphorus, Sulfur, and Silicon and the Related Elements, Polysulfonylamine: Teil Lvi.1 Dimesylaminosulfonylisocyanat: Additionsreaktionen Mit Oh-, Sh- Und Nh-Funktionellen Molekülen; Festkörperstruktur Von N-(Dimesylaminosulfonyl)-Methylurethan, vol. 86, pp. 85-92, 2006, USA.

* cited by examiner

*Primary Examiner* — Alexander Usyatinsky
(74) *Attorney, Agent, or Firm* — True Shepherd LLC; Andrew C. Cheng

(57) ABSTRACT

An isocyanate electrolyte solution additive containing a sulfamide structural group has a structure of formula I:

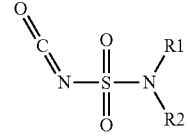

Formula I where $R_1$ and $R_2$ are identical or different, $R_1$ and $R_2$ are each independently selected from methyl, ethyl, butyl, methoxy, methanesulfonyl, ethanesulfonyl, fluorosulfonyl, trifluoromethanesulfonyl, perfluoroethylsulfonyl, benzenesulfonyl, alkyl-containing benzenesulfonyl, cyano/fluorobenzenesulfonyl and alkoxy-containing benzenesulfonyl, and $R_1$ and $R_2$ can be linked to form one of five-membered ring or six-membered ring.

6 Claims, No Drawings

ELECTROLYTE SOLUTION ADDITIVE CONTAINING ISOCYANATE AND SULFAMIDE STRUCTURAL GROUPS AND APPLICATION THEREOF

CROSS-REFERENCE TO RELATED APPLICATIONS

This application is a continuation of International Patent Application No. PCT/CN2022/078800 with a filing date of Mar. 2, 2022, designating the United States, now pending, and further claims priority to Chinese Patent Application No. 202111400107.1 with a filing date of Nov. 24, 2021. The content of the aforementioned applications, including any intervening amendments thereto, are incorporated herein by reference.

TECHNICAL FIELD

The present disclosure relates to an isocyanate electrolyte solution additive containing a sulfamide structural group and application thereof, belonging to the technical field of a non-aqueous electrolyte solution additive of a lithium battery.

BACKGROUND

Since its commercialization, a lithium secondary battery has been widely applied to the fields of digitals, energy storage, power, military aerospace and communication equipment due to its high specific energy and good cycle performance. Compared with other secondary batteries, the lithium secondary battery has the advantages of high working voltage, long cycle life, low self-discharge rate, environmental friendliness, no memory effect and the like.

In a lithium ion battery, the performance of the battery seriously declines because of the performance of the electrolyte solution to oxidize, decompose and degrade the battery along with the dissolution of metal ions in the process of cycle and high temperature storage. With the continuous increase of market demands on the lithium ion battery, higher requirements are provided to the comprehensive performance demand of the battery, and therefore use of an additive is an effective way to improve the comprehensive performance of the lithium ion battery. However, there are various kinds of additives, including a film forming additive, an overcharge protection additive, a conductive additive, a flame retardant additive, an electrolyte solution stabilizer and the like according to different functions of the additives in the electrolyte solutions. Regardless of the additive, it accounts for a small proportion of the electrolyte solution, but is widely researched and developed due to its obvious functions.

The traditional lithium secondary battery adopts a carbonic ester electrolyte solution that forms an interface film on the surfaces of the cathode and the anode, which is not conducive to the transport of lithium ions to lead to the attenuation of electrochemical performances of the battery caused by too high impedance of the interface film. The film forming additive can be used as an effective means to improve the performance of the interface film of the cathode and the anode, wherein the impedance property is considered as an important characteristic of the interface film, and therefore the film forming additive is expected to be developed to reduce the impedance of the interface film of the anode and the cathode of the lithium secondary battery.

Generally speaking, sulfur-containing additives can reduce the impedance of the battery to a certain extent, so as to improve the high temperature performance and the low temperature performance of the battery. 1,3-propane sulfonate lactone (PS) and ethylene sulfate (DTD), as representative sulfur-containing additives, are film forming additives having the effect of reducing the impedance of the battery. However, 1,3-propane sulfonate lactone (PS) is limited in use due to regulation under EU laws; ethylene sulfate (DTD) is poor in thermostability, if a stabilizing agent is absent, it will result in the degradation of the acid value and chroma of the electrolyte solution, thereby affecting the high temperature performance of the battery.

Hence, it is important to develop a novel film forming additive and an electrolyte stabilizing agent.

SUMMARY OF PRESENT INVENTION

Aiming at the defects in the prior art, the present disclosure provides an isocyanate electrolyte solution additive having good thermostability. The additive has a good impedance reducing effect, and is capable of forming a stable interface film on the surface of an electrode, thereby achieving the purpose of improving the property of the interface.

To solve the above technical problem, the present disclosure provides the following technical solution: an isocyanate electrolyte solution additive containing a sulfamide structural group is provided, the electrolyte solution additive having a structure of formula I:

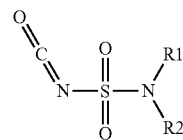

Formula I where Q=$R_1$ and $R_2$ which are identical or different, $R_1$ and $R_2$ are each independently selected from one of methyl, ethyl, butyl, methoxy, methanesulfonyl, ethanesulfonyl, fluorosulfonyl, trifluoromethanesulfonyl, perfluoroethylsulfonyl, benzenesulfonyl, alkyl-containing benzenesulfonyl, cyano/fluorobenzenesulfonyl and alkoxy-containing benzenesulfonyl, and $R_1$ and $R_2$ can be linked to form one of a five-membered ring or a six-membered ring.

The compound structure of the isocyanate electrolyte solution additive containing the sulfamide structural group and a preparation method thereof have been reported in documents as follows: J. Org. Chem. 1994, 59, 3540-3542; CN1039417; CN1033807; Phosphorus, Sulfur, and Silicon, 1992, 70, 91-97, in which such the materials have been discussed.

In one embodiment, the electrolyte solution additive is any one or a mixture of two or more selected from a group consisting of the following structural formulas:

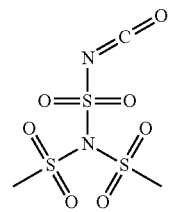

SN-01

-continued
SN-02
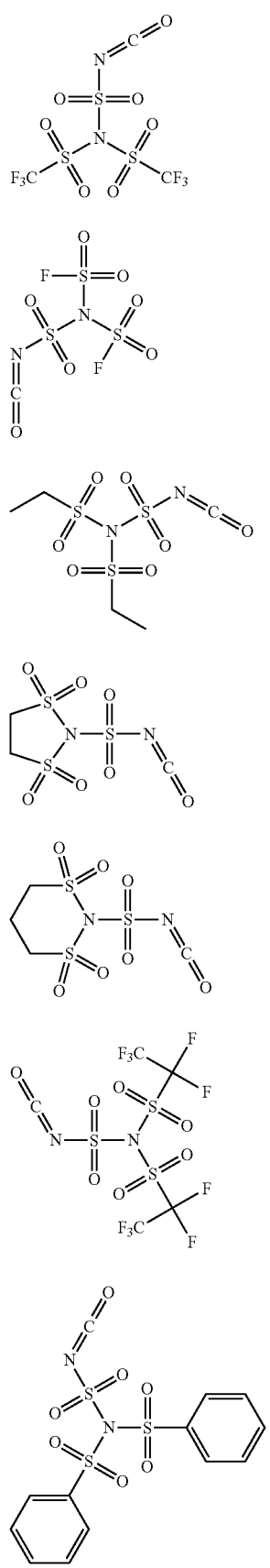
SN-03
SN-04
SN-05
SN-06
SN-07
SN-08
-continued
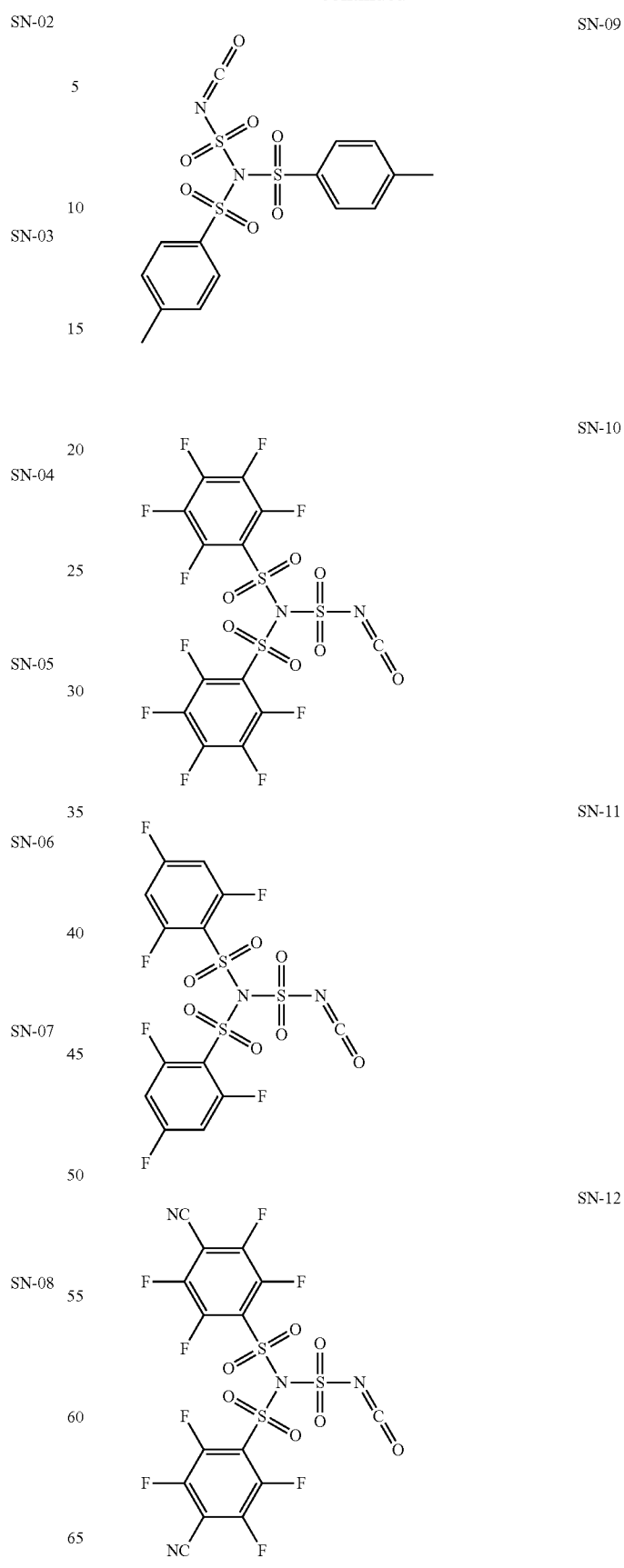
SN-09
SN-10
SN-11
SN-12

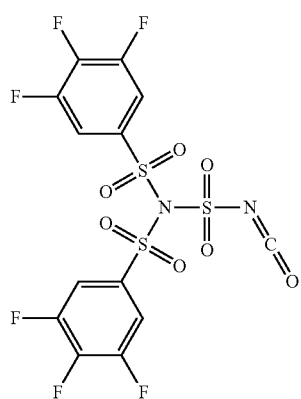 SN-13
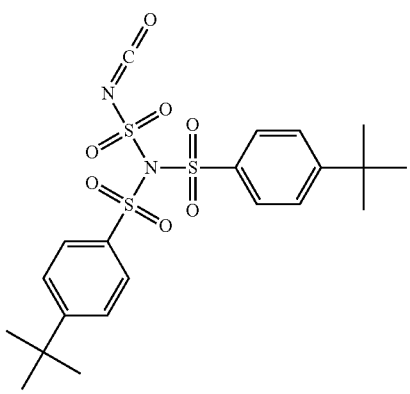 SN-17
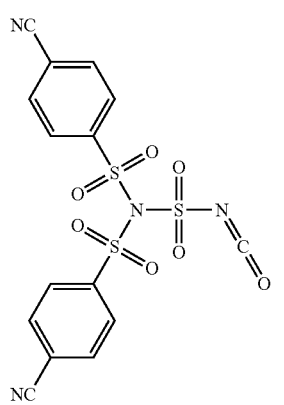 SN-14
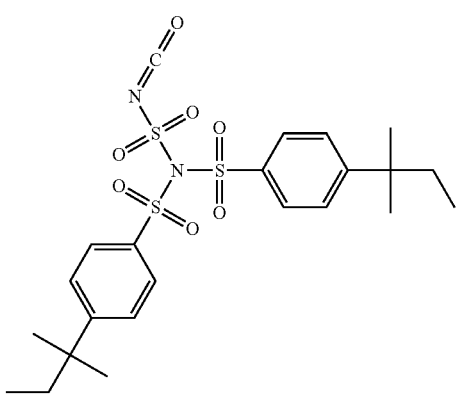 SN-18
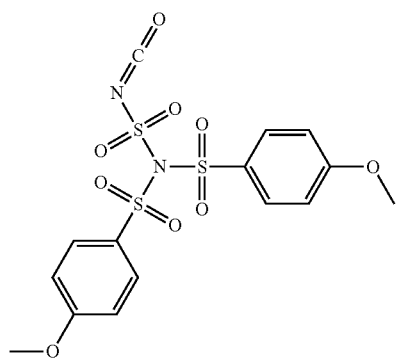 SN-15
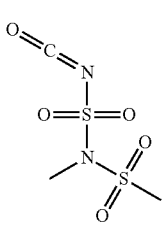 SN-19
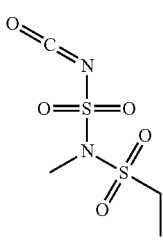 SN-20
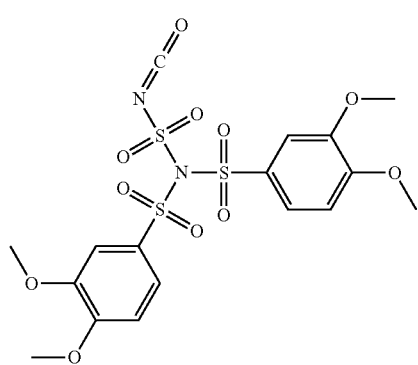 SN-16
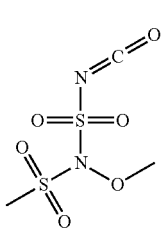 SN-21

SN-22

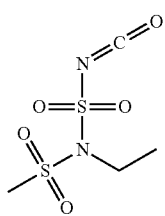

SN-23

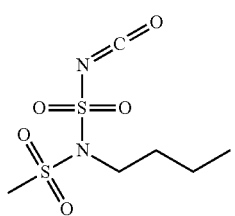

SN-25

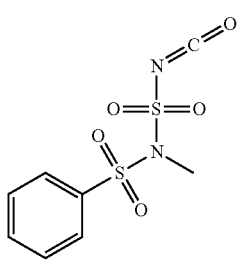

SN-27

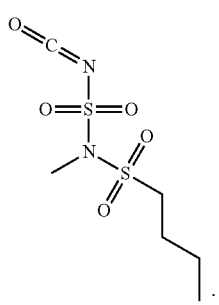

The isocyanate electrolyte solution additive containing the sulfamide structural group provided by the present disclosure has good thermostability, and can be stored for 30 days at the high temperature of 45° C. after being prepared into a lithium ion battery non-aqueous electrolyte solution, but the prepared electrolyte solution is stable in acid value and chrome. When the novel additive provided by the present disclosure patent is mixed with ethylene sulfate (DTD) or methylene methane disulfonate (MMDS) to prepare the electrolyte solution, it can play a role in a DTD or MMDS stabilizing agent, so as to effectively inhibit the increase in the acidity and the chrome of the electrolyte solution, thereby promoting the relevant performances of the battery.

The present disclosure further discloses an application of the isocyanate electrolyte solution additive containing the sulfamide structural group. The isocyanate electrolyte solution additive containing the sulfamide structural group can be applied to a lithium ion battery, the lithium ion battery comprises an anode, a cathode, a diaphragm arranged between the anode and the cathode and an electrolyte solution.

The anode is any one or a mixture of two or more selected from a group consisting of a carbon-based active material, a silicon-based active material, a metal-based active material and a lithium-containing nitride.

In one embodiment, the electrolyte solution comprises a solvent, an electrolyte lithium salt and an additive. The additive at least comprises the isocyanate electrolyte solution additive containing the sulfamide structural group.

In one embodiment, a content of the isocyanate electrolyte solution additive containing the sulfamide structural group is 0.01 wt %-5 wt % of a total weight of the electrolyte solution, preferably 0.05 wt %-1 wt %.

In one embodiment, the electrolyte lithium salt is one or more selected from a group consisting of $LiPF_6$, $LiClO_4$, $LiBF_4$, LiBOB, LiODFB, LiTDI, LiTFSI and LiFSI. A content of the electrolyte lithium salt is 10 wt %-20 wt % of the total weight of the electrolyte solution.

In one embodiment, the solvent is any one or a combination of two or more selected from a group consisting of ethylene carbonate, propylene carbonate, butylene carbonate, ethylene fluorocarbonate, dimethyl carbonate, diethyl carbonate, dipropyl carbonate, ethylmethyl carbonate, methylpropyl carbonate, ethylpropyl carbonate, methylpropargyl carbonate, 1,4-butylrolactone, methyl propionate, methyl butyrate, ethyl acetate, ethyl propionate, propyl propionate or ethyl butyrate.

The present disclosure has the beneficial effects:

(1) in the isocyanate electrolyte solution additive containing the sulfamide structural group provided by the present disclosure, the isocyanate group has strong electrophilic activity, can act with moisture in the electrolyte solution system and active hydrogen contained in the anode and the cathode, so as to reduce $LiPF_6$ decomposition caused by active hydrogen.

(2) In the novel additive provided by the present disclosure, the sulfamide group has good film forming performance, the addition of the sulfamide group into the electrolyte solution can form a stable interface film on the surface of the electrode; furthermore, the sulfamide structural group brings element S into an solid electrolyte interface (SEI) film so as to increase the ion conductivity, and therefore the cycle performance of the lithium ion battery can be effectively improved, which is specifically reflected in a fact that the battery has good cycle performance while exhibiting low internal resistance.

(3) In the novel additive provided by the present disclosure, the sulfamide group and the isocyanate structural group are organically combined, so that the novel additive shows good thermostability, plays a role in an electrolyte solution stabilizing agent, and avoids the high temperature discoloration and acid value increase of the electrolyte solution. Even though the novel additive provided by the present disclosure is applied to the electrolyte solution system containing ethylene sulfate (DTD) or methylene methane disulfonate (MMDS) which is prone to causing the increase in the acid value and the chrome of the electrolyte solution, it also shows a good effect of an electrolyte solution stabilizing agent, so as to effectively inhibit the discoloration and acid value increase of the electrolyte solution. The application of the novel additive provided by the present disclosure patent to the battery improves the high temperature recycle and the high temperature storage performance, and the low impedance is exhibited.

DETAILED DESCRIPTION OF THE EMBODIMENTS

To make the above objective, features and advantages of the present disclosure more clear and understandable, specific embodiments of the present disclosure will be described in detail below. The following description explains many specific details so as to sufficiently understand the present disclosure. However, the present disclosure can be implemented in many other ways different from the description herein. Similar modifications can be made by those skilled in the art without departing from the spirit of the present disclosure, and therefore the present disclosure is not limited by specific embodiments disclosed hereinafter.

Unless otherwise defined, all technical and scientific terms used herein have the same meaning as those commonly understood by those skilled in the technical field of the present disclosure. The terms used in the specification of the present disclosure in this document are only for the purpose of describing the specific embodiments, and are not intended to limit the present disclosure.

Battery Examples

Formulations of lithium ion battery non-aqueous electrolyte solutions listed in battery examples 1-8 and comparative examples 1-5 are shown in Table 1.

TABLE 1

Formulations of lithium ion battery non-aqueous electrolyte solutions listed in battery examples 1-8 and comparative examples 1-5

| Number | Cathode material of battery | Isocyanate additive provided by the present disclosure | Other additives | Electrolyte lithium salt | Ethylene carbonate: dimethyl carbonate:methyl ethyl carbonate (weight ratio %) |
|---|---|---|---|---|---|
| Example 1 | $LiNi_{0.8}Co_{0.1}Mn_{0.1}O_2$ | 0.75% SN02 | / | 13.5% $LiPF_6$ | 30:40:30 |
| Example 2 | $LiNi_{0.8}Co_{0.1}Mn_{0.1}O_2$ | 0.5% SN03 | / | 13.5% $LiPF_6$ | 30:40:30 |
| Example 3 | $LiNi_{0.8}Co_{0.1}Mn_{0.1}O_2$ | 1.0% SN11 | / | 13.5% $LiPF_6$ | 30:40:30 |
| Example 4 | $LiNi_{0.8}Co_{0.1}Mn_{0.1}O_2$ | 0.5% SN19 | / | 13.5% $LiPF_6$ | 30:40:30 |
| Example 5 | $LiNi_{0.8}Co_{0.1}Mn_{0.1}O_2$ | 0.5% SN02 | 1.0% 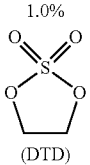 (DTD) | 13.5% $LiPF_6$ | 30:40:30 |
| Example 6 | $LiNi_{0.8}Co_{0.1}Mn_{0.1}O_2$ | 0.1% SN03 | 1.0% 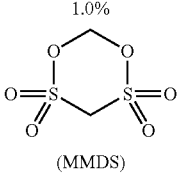 (MMDS) | 13.5% $LiPF_6$ | 30:40:30 |
| Example 7 | $LiNi_{0.8}Co_{0.1}Mn_{0.1}O_2$ | 0.25% SN11 | 1.0% 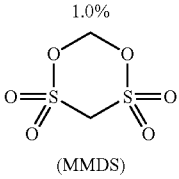 (MMDS) | 13.5% $LiPF_6$ | 30:40:30 |
| Example 8 | $LiNi_{0.8}Co_{0.1}Mn_{0.1}O_2$ | 0.75% SN19 | 1.0% 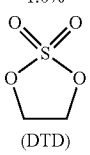 (DTD) | 13.5% $LiPF_6$ | 30:40:30 |
| Comparative example 1 | $LiNi_{0.8}Co_{0.1}Mn_{0.1}O_2$ | / | / | 13.5% $LiPF_6$ | 30:40:30 |
| Comparative example 2 | $LiNi_{0.8}Co_{0.1}Mn_{0.1}O_2$ | / | 1.0% 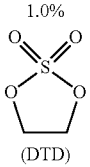 (DTD) | 13.5% $LiPF_6$ | 30:40:30 |

TABLE 1-continued

Formulations of lithium ion battery non-aqueous electrolyte solutions listed in battery examples 1-8 and comparative examples 1-5

| Number | Cathode material of battery | Isocyanate additive provided by the present disclosure | Other additives | Electrolyte lithium salt | Ethylene carbonate: dimethyl carbonate:methyl ethyl carbonate (weight ratio %) |
|---|---|---|---|---|---|
| Comparative example 3 | $LiNi_{0.8}Co_{0.1}Mn_{0.1}O_2$ | / | 1.0% (MMDS) | 13.5% $LiPF_6$ | 30:40:30 |
| Comparative example 4 | $LiNi_{0.8}Co_{0.1}Mn_{0.1}O_2$ | / | 0.5% 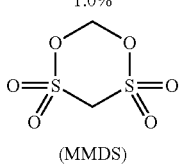 + 1.0% | 13.5% $LiPF_6$ | 30:40:30 |
| Comparative example 5 | $LiNi_{0.8}Co_{0.1}Mn_{0.1}O_2$ | / | 0.5% 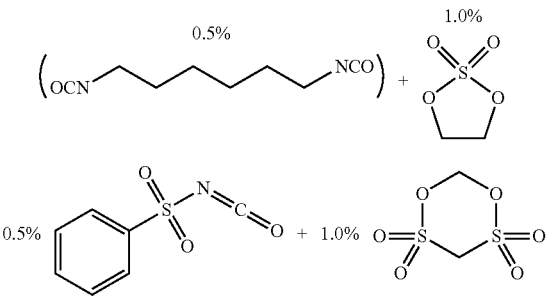 + 1.0% | 13.5% $LiPF_6$ | 30:40:30 |

A method for preparing a lithium ion button battery by using the lithium ion battery non-aqueous electrolyte solutions in battery examples 1-8 and comparative examples 1-5 is as follows:

(1) Preparation of Cathode Plate

Cathode $LiNi_{0.8}Co_{0.1}Mn_{0.1}O_2$ powders, carbon black (particle size: 1000 nm), polyvinylidene fluoride (PVDF) and N,N-dimethyl pyrrolidone (NMP) were mixed to prepare uniform slurry, the slurry was evenly coated onto an aluminum foil (15 μm) current collector, and then dried and rolled, so as to obtain a $LiNi_{0.8}Co_{0.1}Mn_{0.1}O_2$ cathode material. After drying for 12 hours at 120° C., in the dried electrode plate, $LiNi_{0.8}Co_{0.1}Mn_{0.1}O_2$ accounted for 94% of a total coating material, a binder accounted for 4% of the total coating material, and carbon black accounted for 2% of the total coating material. Then, the obtained electrode plate was cut into a wafer with a diameter of 8 mm as a cathode.

(2) Preparation of Anode Plate

An artificial graphite anode material was taken as an example: artificial graphite, polyvinylidene fluoride (PVDF) and N-methylpyrrolidone (NMP) were mixed to prepare uniform slurry, and the slurry was evenly coated onto a copper foil (15 μm) current collector, and then dried and rolled to obtain a carbon anode material. After drying for 12 hours at 120° C., in the dried electrode plate, the graphite accounted for 96.4% of a total coating material, a binder accounted for 3.6% of the total coating material. Then, the obtained electrode plate was cut into wafer with a diameter of 8 mm as an anode.

(3) Preparation of Electrolyte Solution

In an argon atmosphere glove box containing <1 ppm of water, a lithium salt was dissolved into a solvent, then novel phosphine isocyanate was added, and then the above materials were evenly mixed to obtain the electrolyte solution.

(4) Preparation of Lithium Ion Battery

A CR2430 button battery was assembled by using the materials described in the above steps (1) and (2) as working electrodes, and a Celgard 2400 membrane (Tianjin) as a diaphragm. From the anode to the cathode, the assembling sequence was as follows: an anode shell, a spring piece, a gasket, an anode plate, an electrolyte solution, a diaphragm, a cathode plate, a cathode shell, and then a sealing machine was used for sealing. These operations were all completed in a pure argon glove box, and subsequently the CR2430 button battery was subjected to electrochemical performance test after standing for 6 hours.

Performance Test of Lithium Ion Battery

Test I: stability test of electrolyte solution: the lithium ion battery electrolyte solutions prepared in examples 1-8 and comparative examples 1-5 were respectively put into sealed aluminum bottles, the aluminum bottles were vacuum encapsulated with aluminum-plastic films, and electrolyte solution samples were simultaneously stored in incubators with a set temperature of 45° C. Before storage and after storage for 30 days, the samples were taken from the glove box to detect the acidity and chroma values of the electrolyte solutions. The acidity was measured by a potentiometric titrator. The acidity value is converted into HF, unit: ppm. The chroma is determined by platinum-cobalt colorimetry, unit: Hazen. The test results are shown in Table 2.

TABLE 2

Influence of additive on acid value and chroma of electrolyte solution

| Number | Chroma (Hazan) Before storage | Chroma (Hazan) Store for 30 days | Acidic value (ppm) Before storage | Acidic value (ppm) Store for 30 days |
|---|---|---|---|---|
| Electrolyte solution in example 1 | 10 | 18 | 7.6 | 12.1 |
| Electrolyte solution in example 2 | 10 | 12 | 7.3 | 10.4 |
| Electrolyte solution in example 3 | 10 | 20 | 8.0 | 13.2 |
| Electrolyte solution in example 4 | 10 | 15 | 7.6 | 11.6 |
| Electrolyte solution in example 5 | 10 | 31 | 8.1 | 17.2 |
| Electrolyte solution in example 6 | 10 | 23 | 9.2 | 18.7 |
| Electrolyte solution in example 7 | 10 | 29 | 8.2 | 18.8 |
| Electrolyte solution in example 8 | 10 | 34 | 5.9 | 18.7 |
| Electrolyte solution in example 9 | 10 | 83 | 7.3 | 38.3 |
| Electrolyte solution in comparative example 2 | 10 | 251 | 8.1 | 178.6 |
| Electrolyte solution in comparative example 3 | 10 | 280 | 7.4 | 199.1 |
| Electrolyte solution in comparative example 4 | 10 | 73 | 6.9 | 59.2 |
| Electrolyte solution in comparative example 5 | 10 | 68 | 7.8 | 67.3 |

It can be seen from Table 2 that the electrolyte solutions in examples 1-8 can be stored for 30 days at the high temperature of 45° C., the acidity and chroma of the electrolyte solution are both lower than those in comparative examples, the acidity and chroma of the electrolyte solution are effectively inhibited even though the novel additive provided by the present disclosure is added into the electrolyte solution systems of ethylene sulfate (DTD) or methylene methane disulfonate (MMDS), so that the acidity and chroma of the electrolyte solution can be effectively inhibited by adding the novel additive provided by the present disclosure. Accordingly, the novel additive provided by the present disclosure can effectively inhibit the increase in the acidity and chroma of the electrolyte solution and improve the stability of the electrolyte solution under high-temperature conditions.

Test II: high temperature cycle performance test and high temperature storage performance test The prepared batteries respectively underwent the following tests:

① at 45° C., the battery was charged to 4.3 V at a constant current of 0.1 C, and then discharged to 2.7 V at a constant current of corresponding magnification. This was the first cycle;

② after the first cycle was ended, the battery was charged to 4.3 V at a constant current at 1.0 C, and then discharged to 2.7 V at a constant current at the corresponding rate. The tests of 100 and 500 cycles were respectively performed according to the cycle conditions, and the capacity retention rates of the battery after 100 and 500 cycles were calculated respectively. Wherein, the capacity retention rate after the cycle is calculated according to the following formula. Relevant test data obtained from each battery is shown in Table 2;

Capacity retention rate after cycle=(discharge capacity after the corresponding number of cycles/discharge capacity of the first cycle)×100%.

High temperature storage internal resistance change rate test: five charge-discharge cycle tests were performed at room temperature at the rate of 1 C for the batteries in examples 1-8 and comparative examples 1-5, and filially charged to the full charge state at the rate of 1 C. The battery internal resistance T was recorded. The fully charged battery was stored at 60° C. for 15 days, the internal resistance T0 of the battery was recorded, and the change rate of the internal resistance of the battery and other experimental data were calculated. The results are recorded and shown in Table 3 (the numbers of batteries in example 1-8 are respectively battery 1-battery 8, and the numbers of batteries in comparative examples 1-5 are respectively battery 1#-battery 5#).

Change rate of internal resistance=$(T-T0)/T\times100\%$.

TABLE 3

Test results of examples and comparative examples

| Number of battery | Capacity retention rate/% 100 weeks | Capacity retention rate/% 500 weeks | Change rate % of internal resistance after storage for 15 days at 60° C. |
|---|---|---|---|
| Battery 1 | 93.37 | 83.49 | 5.3 |
| Battery 2 | 94.24 | 8619 | 4.4 |
| Battery 3 | 89.89 | 82.49 | 5.3 |
| Battery 4 | 92.73 | 84.13 | 4.9 |
| Battery 5 | 92.38 | 83.67 | 5.1 |
| Battery 6 | 94.31 | 82.49 | 4.3 |
| Battery 7 | 93.39 | 86.31 | 5.0 |
| Battery 8 | 94.05 | 85.93 | 4.8 |
| Battery 1# | 68.59 | 46.39 | 8.9 |
| Battery 2# | 79.69 | 68.62 | 7.7 |
| Battery 3# | 78.98 | 67.34 | 8.1 |
| Battery 4# | 86.25 | 75.25 | 7.3 |
| Battery 5# | 80.32 | 74.39 | 7.6 |

It can be seen from Table 3 that the use of the novel additive of the present disclosure can significantly improve the high-temperature cycle performance and the high temperature impedance performance of the lithium secondary battery. It is proved that by the improvement of the interface property of the anode electrode/electrolyte solution, the novel additive of the present disclosure can reduce the irreversible capacity of the lithium secondary battery during the first charge and discharge and maintain the stability of the interface while reducing the interface impedance, and is helpful to improve the high temperature cycle stability of the lithium secondary battery.

Accordingly, the novel additive of the present disclosure has good thermostability, can play a role in an electrolyte solution stabilizing agent and avoids the high temperature discoloration and the acid value increase of the electrolyte solution. Even though the novel additive provided by the present disclosure patent is applied to the electrolyte system containing ethylene sulfate (DTD) or methylene methane disulfonate (MMDS) that is prone to the increase in the acid value and chroma of the electrolyte solution, it also shows a good electrolyte stabilizing agent effect, thereby effectively inhibiting the discoloration and acid value increase of the electrolyte solution. After the electrolyte solution containing the novel additive provided by the present disclosure patent is applied to the battery, the battery has improved high temperature cycle performance and low impedance, and therefore the additive has a good application prospect.

Various technical features of the above embodiments can be randomly combined. To make the description concise, all possible combinations of technical features in the above embodiments are not described, however, as long as the combinations of these technical features are not contradictory, they should be considered to be included within the scope of the specification.

The above embodiments are only for expressing several embodiments of the present disclosure, the descriptions are more specific and detailed, but cannot be understood as limiting the scope of the disclosure patent. It should be noted that several deformations and improvements can be made by persons of ordinary skill in the art without departing from the idea of the present disclosure, all of which are included within the protective scope of the present disclosure. Therefore, the protective scope of the present disclosure patent shall be subject to the attached claims.

What is claimed is:

1. An electrolyte solution additive containing isocyanate compound and sulfamide structural groups,
wherein the electrolyte solution additive is one or a mixture of two or more selected from a group consisting the following structural formulas:

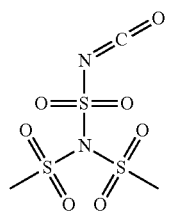

SN-01

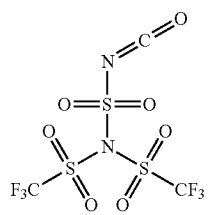

SN-02

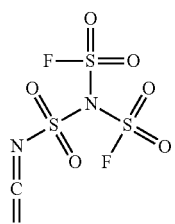

SN-03

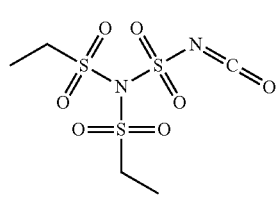

SN-04

-continued

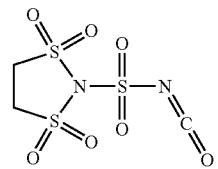

SN-05

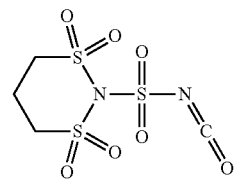

SN-06

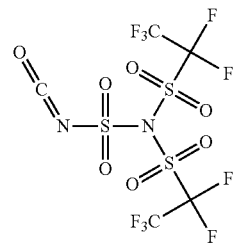

SN-07

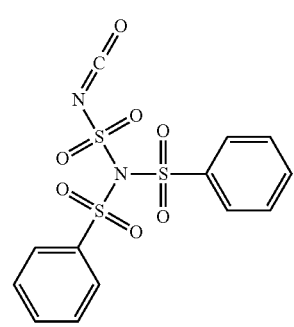

SN-08

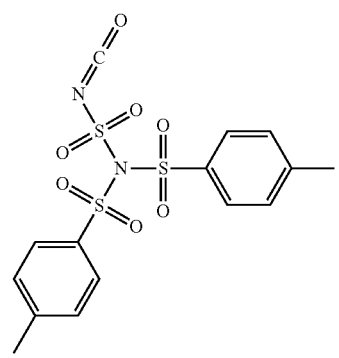

SN-09

-continued

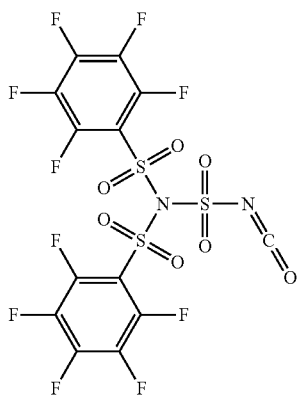
SN-10

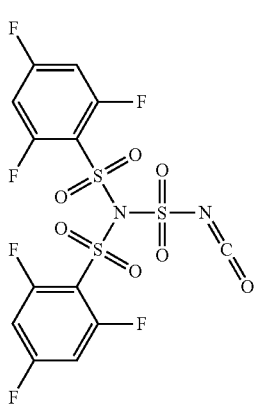
SN-11

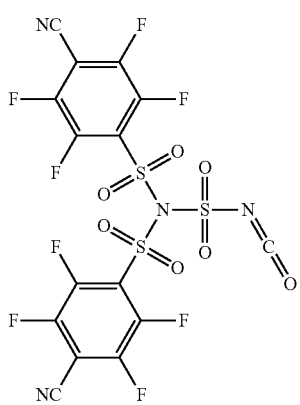
SN-12

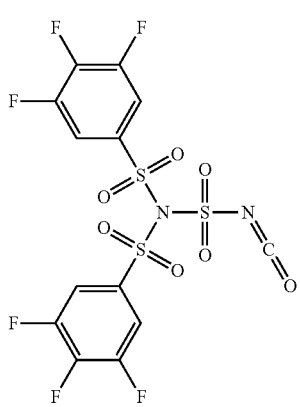
SN-13

-continued

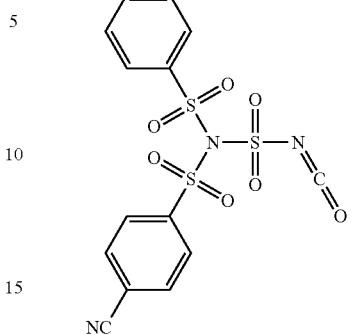
SN-14

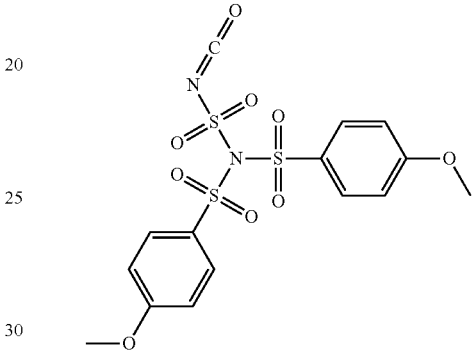
SN-15

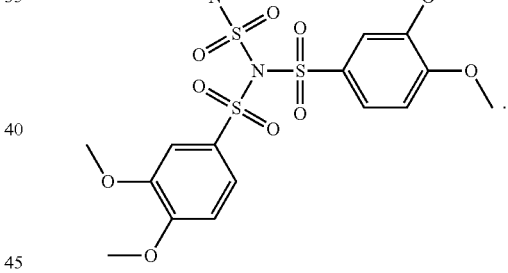
SN-16

2. A lithium ion battery, wherein the electrolyte solution additive containing the isocyanate compound and sulfamide structural groups according to claim 1 is applied to the lithium ion battery, the lithium ion battery comprises an anode, a cathode, a diaphragm arranged between the cathode and the anode and an electrolyte solution.

3. The lithium ion battery according to claim 2, wherein the electrolyte solution comprises a solvent, an electrolyte lithium salt and an additive, and the additive at least comprises the electrolyte solution additive containing the isocyanate compound and sulfamide structural groups.

4. The lithium ion battery according to claim 3, wherein a content of the electrolyte solution additive containing the isocyanate compound and sulfamide structural groups is 0.01wt %-5wt % of a total weight of the electrolyte solution.

5. The lithium ion battery according to claim 3, wherein the electrolyte lithium salt is one or more selected from a group consisting of $LiPF_6$, $LiClO_4$, $LiBF_4$, LiBOB, LiODFB, LITDI, LiTFSI and LiFSI; a content of the electrolyte lithium salt is 10wt %-20wt % of a total weight of the electrolyte solution.

6. The lithium ion battery according to claim 3, wherein the solvent is any one or a combination of two or more selected from a group consisting of ethylene carbonate, propylene carbonate, butylene carbonate, ethylene fluorocarbonate, dimethyl carbonate, diethyl carbonate, dipropyl carbonate, ethylmethyl carbonate, methylpropyl carbonate, ethylpropyl carbonate, methylpropargyl carbonate, 1,4-butylrolactone, methyl propionate, methyl butyrate, ethyl acetate, ethyl propionate, propyl propionate and ethyl butyrate.

\* \* \* \* \*